United States Patent [19]

Lynn

[11] Patent Number: 5,210,994
[45] Date of Patent: May 18, 1993

[54] COLLECTOR FOR A FLUID SAMPLING DEVICE

[76] Inventor: Lewis G. Lynn, 65 Hillhurst La., Rochester, N.Y. 14617

[21] Appl. No.: 825,140

[22] Filed: Jan. 24, 1992

[51] Int. Cl.⁵ .................... B65B 3/06; B65B 39/00
[52] U.S. Cl. .................... 53/469; 53/284.7; 53/390; 141/10; 141/391; 141/313; 248/97; 248/99
[58] Field of Search ............. 53/459, 469, 390, 570, 53/284.7; 248/97, 99, 100; 141/10, 391, 114, 166, 313, 314, 326, 328

[56] References Cited

U.S. PATENT DOCUMENTS

| | | | |
|---|---|---|---|
| 1,580,163 | 4/1926 | Peterson et al. | 248/100 X |
| 2,324,596 | 7/1943 | Quain | 53/390 X |
| 2,900,779 | 8/1959 | Baxter et al. | 53/390 X |
| 3,406,727 | 10/1968 | Rexus | 141/314 X |
| 3,596,430 | 8/1971 | Parish | 53/390 X |
| 3,818,956 | 6/1974 | Chamberlain | 248/99 X |
| 4,344,269 | 8/1982 | Dieterlen et al. | 53/469 X |
| 4,415,085 | 11/1983 | Clarke et al. | 53/390 X |
| 4,774,797 | 10/1988 | Colamussi et al. | 53/459 |
| 5,131,499 | 7/1992 | Hoar | 53/390 X |

*Primary Examiner*—Horace M. Culver
*Attorney, Agent, or Firm*—Shlesinger, Fitzsimmons & Shlesinger

[57] ABSTRACT

The sample collector includes a plurality of like, plastic bags each of which has an opening in one end thereof. The bags are supported over a bag divider rack having thereon a bottom wall, and a plurality of divider plates which project upwardly from said bottom wall and radially of a centerline thereof, so that each pair of adjacent bags is separated by one of said divider plates. An annular spout is removably mounted on each of said divider plates and is releasably secured in the opening in one of the bags operatively to support the opening in position to register with a liquid dispenser to receive a liquid sample therefrom. After being filled the bags are sealed and can be removed individually from the divider rack or the rack itself can be carried with the filled bags positioned thereon.

20 Claims, 4 Drawing Sheets

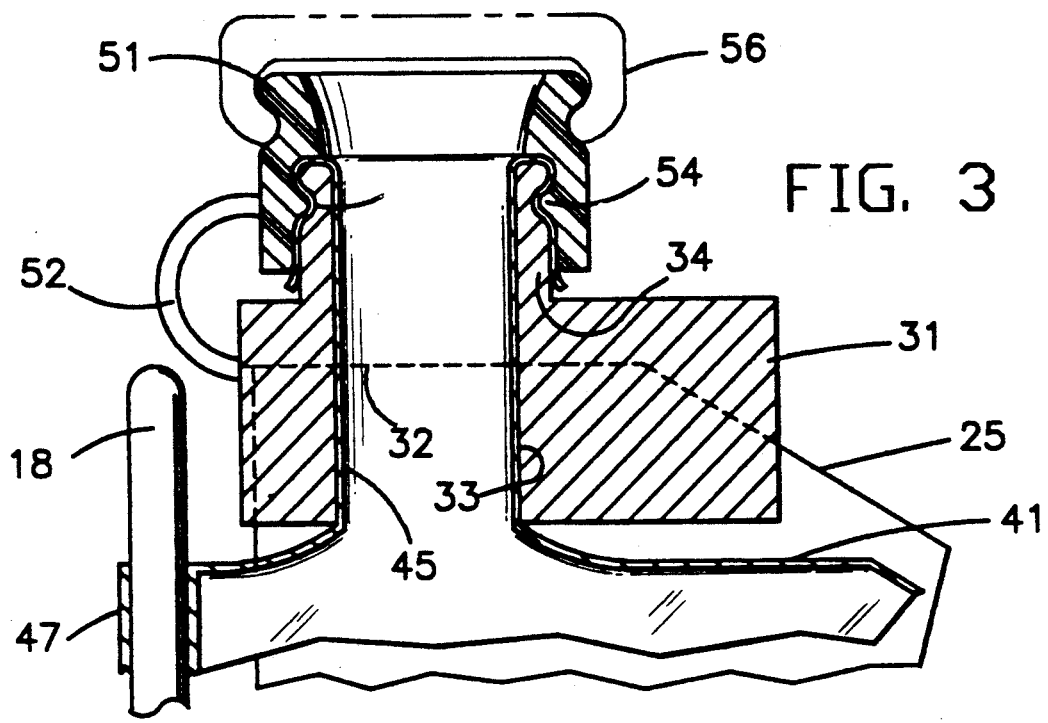
FIG. 3
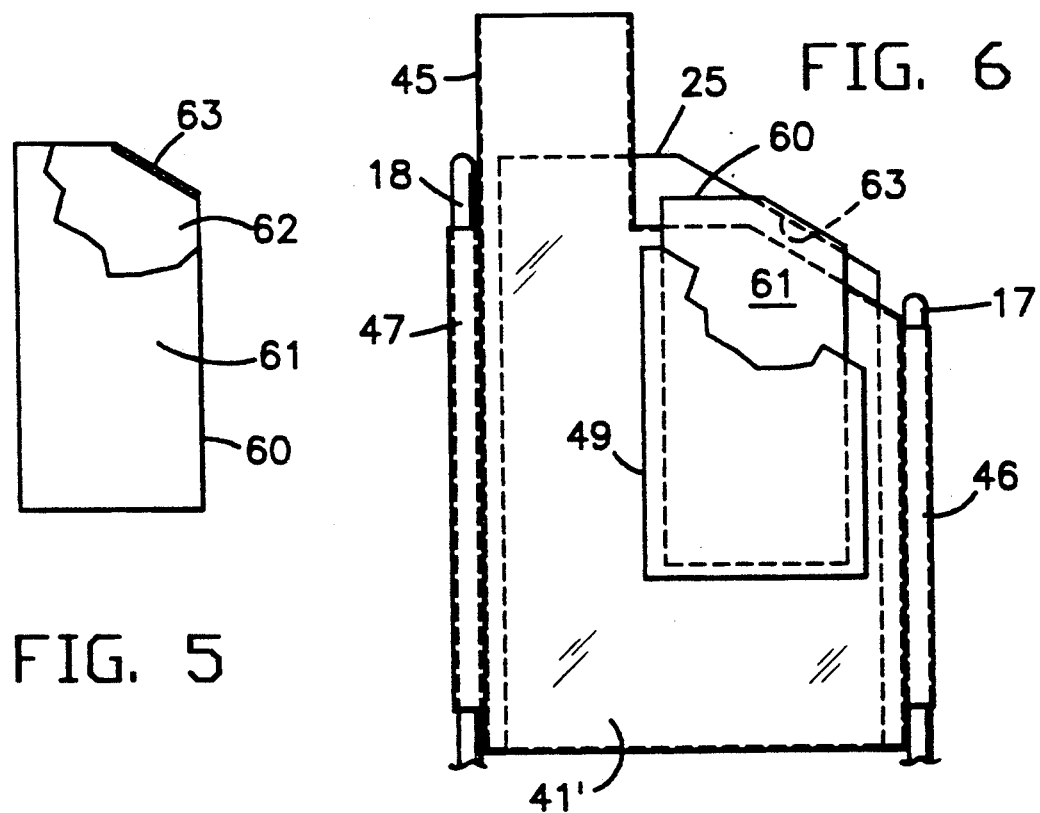
FIG. 5
FIG. 6

COLLECTOR FOR A FLUID SAMPLING DEVICE

BACKGROUND OF THE INVENTION

This invention relates to fluid sampling devices, and more particularly to improved fluid sample collectors for use in such devices. Even more particularly, this invention relates to novel fluid sample containers and their accompanying support racks, which together form the improved sample collector.

Fluid sampling devices may be broken into two general classes, those which are portable and those which have a permanent residence. Although the devices in these classes obviously differ in both size and weight characteristics, they both utilize the same fluid sample storage bottles.

Conventional fluid sampling devices generally utilize sample storage bottles which are intended to be used, for example, in sets of 24, 12, 8, 4, 2 or 1. The bottles for each of these sets vary in size, therefore all of the various bottles must be kept near the fluid sampling device in which they are intended to be used. This does not present a major problem for sampling devices which have permanent locations, however for portable sampling devices, these accessories become bulky and often times inconvenient to transport. Also, after each use the storage bottles must be cleaned in order to prevent contamination of future samples.

It is therefore an object of this invention to provide an improved sample collector which utilizes alternative fluid sample containers that are compact and therefore, not unduly burdensome upon individuals who operate portable fluid sampling devices.

It is also an object of this invention to provide an improved sample collector for use in both portable and immovable fluid sampling devices.

Another object of this invention is to provide an improved sample collector which utilizes alternative fluid sample containers that are disposable and therefore obviate the need for cleansing thereof.

Other objects of this invention will become apparent hereinafter from the specification and from the recital of the appended claims, particularly when read in conjunction with the accompanying drawings.

SUMMARY OF THE INVENTION

An improved fluid sample collector in accordance with this invention comprises a base rack, a divider rack, a plurality of filling spouts and a plurality of pliable fluid sample bags. Both the base rack and the divider rack provide support for the fluid sample bags, and each has handles attached thereto which allow for easy transport for the contents seated thereon. The fluid sample bags are constructed of a pliable, sturdy plastic which may be selected from any one of several materials in order to accommodate a multitude of effluents and to protect the integrity of the fluid sample. Manufacturing of the plastic bags is performed in such a fashion that the bags are present in a continuous strip, which allows a set of bags to remain together during sampling procedures and thereafter. If so desired, the bags may also be separated by simply cutting a web of connective plastic extending between adjacent bags. Means are also provided which allow the filling spout, and therefore the bag attached thereto, releasably to be sealed closed in order to prevent contamination of the sample contained in the bag.

BRIEF DESCRIPTION OF THE DRAWINGS

FIG. 3 is an enlarged, fragmentary sectional view taken generally along the line 3—3 in FIG. 1 looking in the direction of the arrows;

FIG. 5 is a side elevational view of a bag spreader device adapted to be used with a modified form of the sample collector bag, a portion of the spreader device being broken away and shown in section; and FIG. 6 is a fragmentary side elevational view of a modified collector bag as it appears when mounted in the collector with a spreader device of the type shown in FIG. 5.

DETAILED DESCRIPTION OF THE PREFERRED EMBODIMENTS

Figure 1:
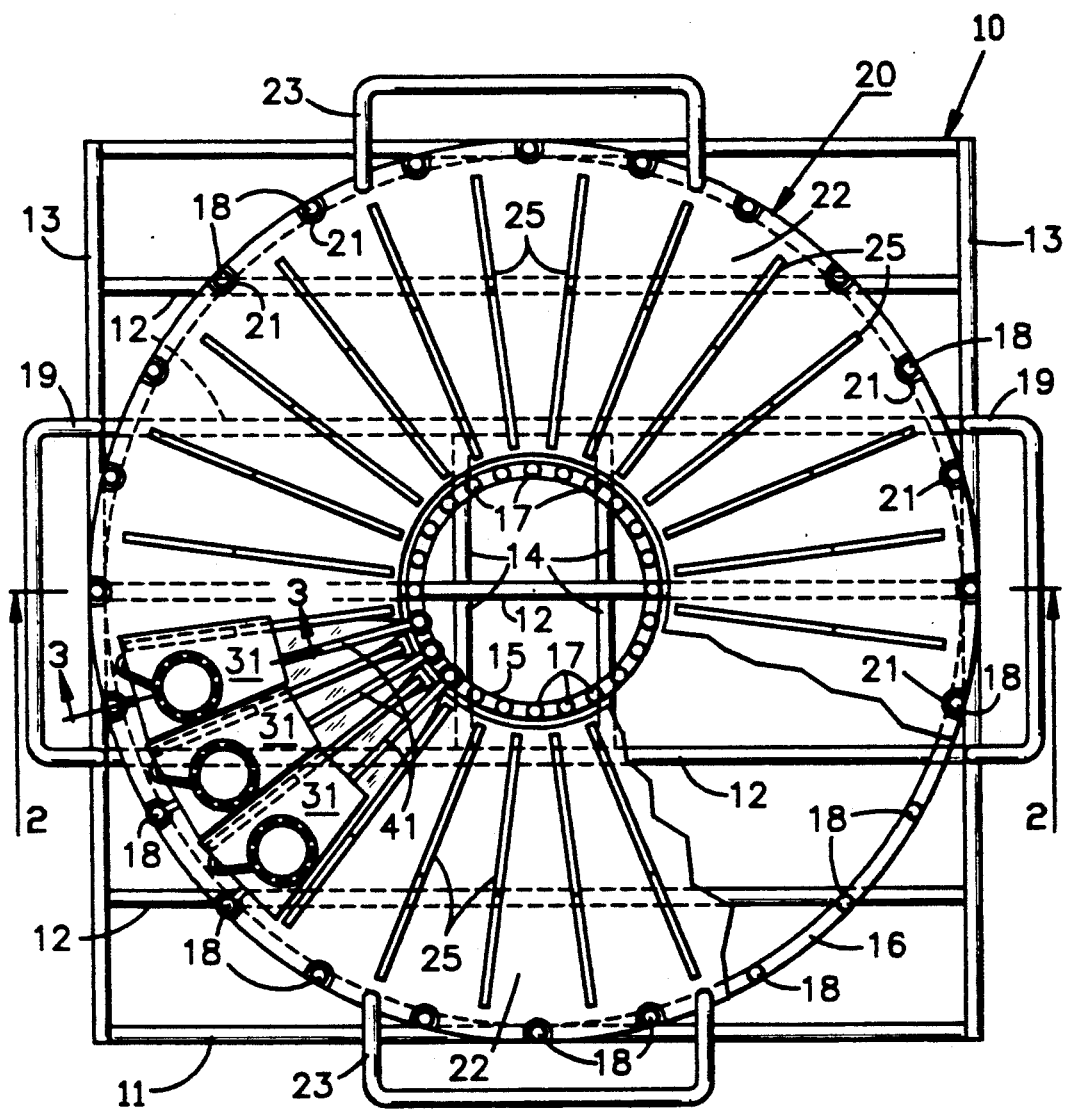
FIG. 1 is a plan view of an improved fluid sample collector made according to one embodiment of this invention, sample collecting bags being shown mounted on the collector's divider rack, and a portion of the divider rack being cut away to expose part of the base rack upon which the divider rack is removably mounted.
Figure 2:
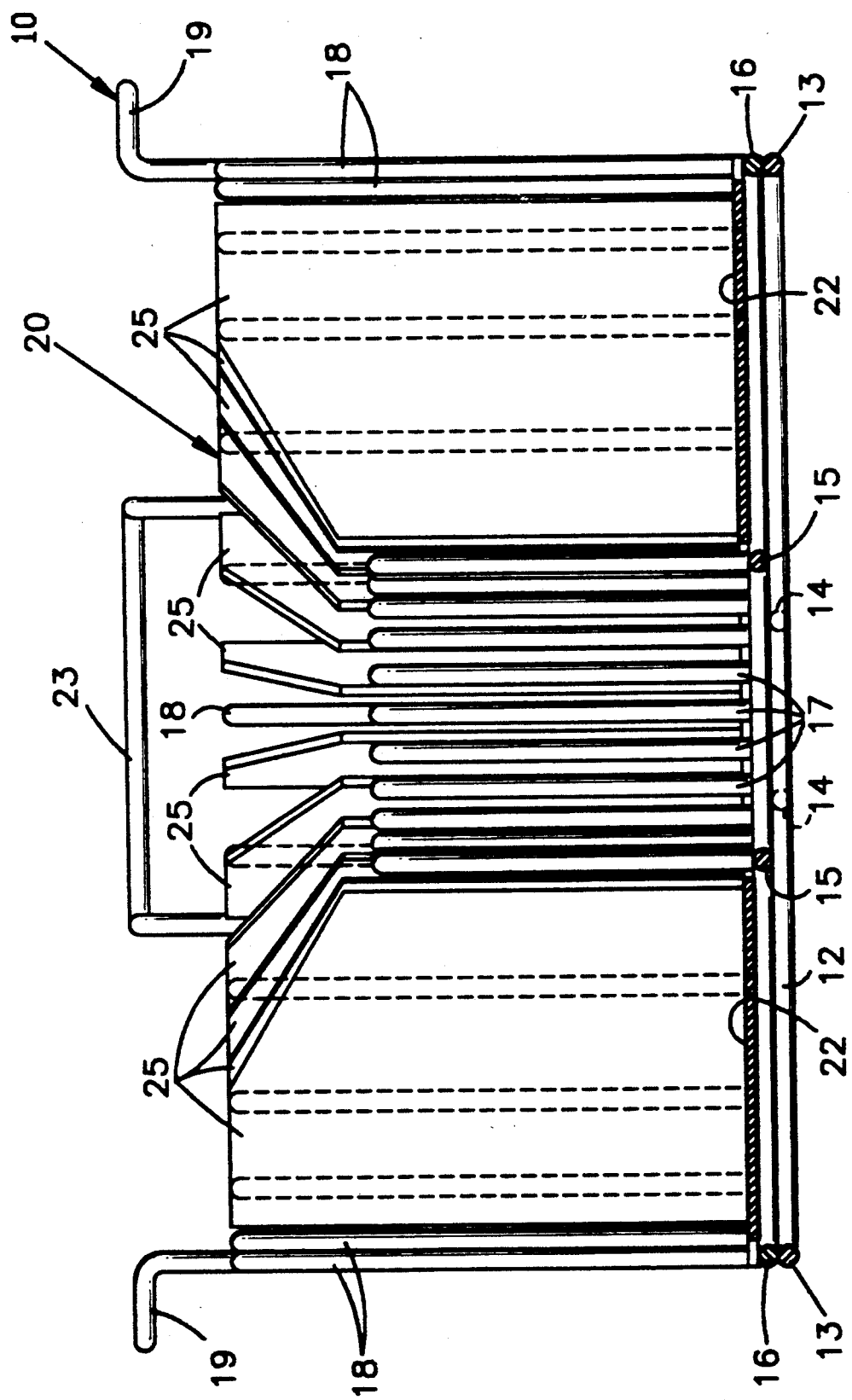
FIG. 2 is a sectional view of this collector taken along the line 2—2 in FIG. 1 looking in the direction of the arrows.

Referring now to the drawings by numerals of reference, and first to FIGS. 1-3, 10 denotes generally a carrying or base rack which forms part of a fluid collector that is designed for use in a conventional fluid sampling device, which is not shown. Rack 10 is made from a plurality of rigid, metal rods, four of which are welded or otherwise secured together to form a square frame 11 reinforced by a further plurality of spaced, parallel, rods 12 that extend transversely between and coplanar with the side rods 13 of frame 11. The innermost rod 12 is connected at diametrally opposite sides thereof to the adjacent rods 12 by shorter, transversely extending rods 14, which also are coplanar with the rods defining frame 11.

Secured upon the upper surfaces of the coplanar rods 12 and 13 centrally of frame 11, and concentrically one within the other, are two, circular rings 15 and 16, each of which is made from a metal rod having the same diameter as rods 12 and 13. Ring 15, which is the smaller of the two rings, has secured to and projecting vertically upwardly from its upper surface a plurality (twenty-four in the embodiment illustrated) of equiangularly spaced, parallel, bag supporting pins or posts 17. Ring 16, which has a diameter approximately equal to the space separating the side rails 13 of frame 11, also has secured to and projecting vertically upwardly from its upper surface outwardly of posts 17 a like plurality (twenty-four) of spaced, parallel bag supporting posts 18, each of which is radially aligned with one of the inner posts 17. Rack 10 can be carried by two handles 19 which project upwardly from the side rails 13 at opposite sides, respectively, of frame 11.

Removably seated centrally on base rack 10 intermediate its bag supporting posts 17 and 18 is divider rack 20. Rack 20 comprises a rigid ring-shaped plate 22 having an inner periphery confronting or bordering on the bag mounting posts 17, and an outer periphery or circumference that has therein a plurality of arcuate notches or recesses 21 which register with and loosely accommodate the bag mounting posts 18. Secured at their lower ends to diametrally opposite sides of plate 22, and projecting upwardly therefrom are two upstanding handles 23. Secured to and projecting vertically upwardly from the upper surface of plate 22 is a plurality (twenty-four) of radially aligned, equi-angularly spaced partitions or divider plates 25. Each divider plate 25 is associated with two adjacent pairs of aligned mounting posts 17 and 18, such that the associated divider 25 is equidistant therebetween. The tops of dividers 25 are inwardly sloped; and the inner mounting posts 17 are shorter than the outer mounting posts 18 in order to allow operation of the conventional fluid sampling equipment (not illustrated), which in use is adapted to overlie the central portion of the fluid sample collector.

Referring now to FIGS. 1 and 3, each divider 25 is disposed to have a wedge-like filler spout 31 removably supported over the upper edge thereof. Each filler spout 31 has in the underside thereof a slot 32 extending the length of its lower surface near one lateral side thereof, and has therethrough an axial bore 33 (FIG. 3). Bore 33 extends at its upper end coaxially through an annular neck 34 which is integral with and which projects upwardly from the upper surface of each spout 31 substantially centrally thereof. Slot 32 is disposed to engage over the top of a divider 25 when a respective filler spout 31 is placed thereon as shown in FIG. 1, whereby its neck 34 and bore 33 are centered between adjacent dividers 25. Neck 34 also has thereon an external circumferential recess or groove 35 for a purpose noted hereinafter.

Figure 4:
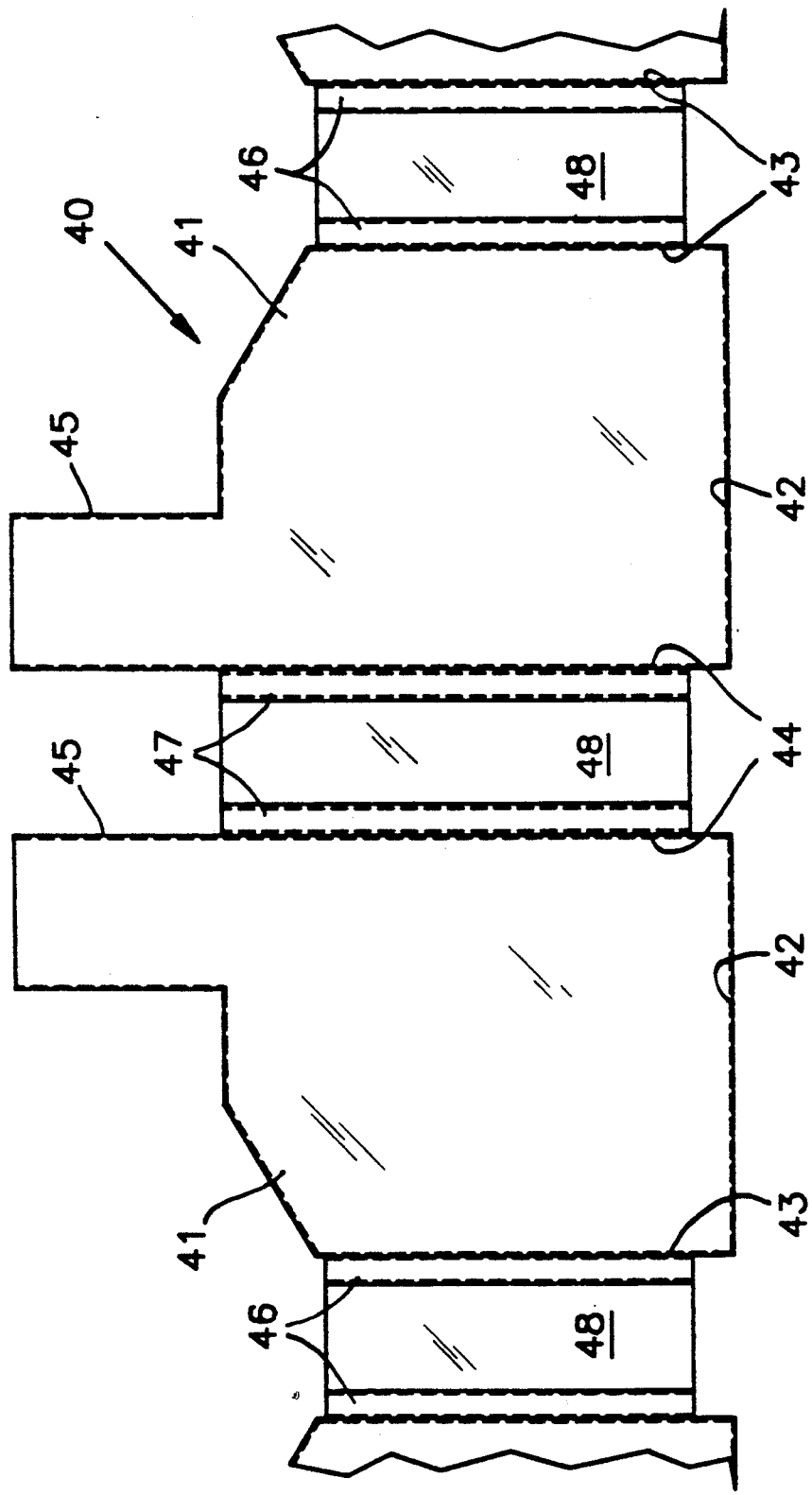
FIG. 4 is a slightly enlarged fragmentary side elevational view of a plurality of successive, interconnected sample collecting bags as they appear after mass production thereof in strip form.

Referring now to FIG. 4, 40 denotes generally part of a strip of watertight, disposable plastic bags as they would appear after manufacture thereof. Each plastic bag 41 in the strip thereof has a closed bottom 42, a short side edge 43, a long side edge 44 and a tubular neck section 45 which projects from the upper end of each bag adjacent its longer side edge 44. Formed along the side edges 43 and 44 of each bag 41 are tubular mounting sleeves 46 and 47, respectively, which as noted hereinafter are disposed to accommodate through their lower ends mounting posts 17 and 18, respectively. As shown, consecutive plastic bags 41 in strip 40 thereof are connected by a web of plastic 48 which extends between the respective sleeves 46 or 47 of adjacent bags.

In use, plastic bags 41 may either be separated by cutting out and removing the connective plastic webs 48 with a knife, scissors or the like; or multiples of the bags (e.g., twenty-four for the illustrated divider rack 20) may remain connected. This allows the user to select whichever option is more convenient. If plastic bags 41 are separated, however, care must be taken to prevent puncturing or otherwise damaging any portion of the bag. To fill the divider rack 20 with bags (see the three sample bags 41 in FIG. 1), each bag 41 is mounted between an adjacent pair of dividers 25 in such manner that the associated mounting posts 17 and 18 are fully inserted into its sleeves 46 and 47, respectively. Once a bag 41 is situated between two dividers 25, a filler spout 31 is placed on top of one of the two dividers 25 adjacent the bag, and such that groove 32 of the filler spout engages over the top portion of the divider. The neck 45 of the bag is then passed upwardly through the bore 33 of the filler spout, and is folded downwardly around the exterior of the filler neck 34.

In order to retain the neck 45 of a respective bag 41 over the tubular neck 34 of a respective filler spout 31, each spout has an annular bag retainer collar 51 loosely attached thereto by a flexible retainer cord 52, one end of which is attached to the exterior of a respective filler spout 31, and the other end of which is attached to the exterior of the associated collar 51. In use, and after the neck 45 of a bag has been folded downwardly over the neck of a filler spout 31, the associated annular collar 51 is forced coaxially downwardly over the upper end of the filler neck 34, as shown for example in FIG. 3, so that an internal, circumferential flange 54 on collar 51 forces an annular portion of the bag neck 45 into the annular recess 35 in the outer periphery of the filler neck 34, thus securing the associated bag 41 in position to be filled by a dispenser (not illustrated) overlying the upper end of collar 51.

Once mounting posts 17 and 18 are fully inserted into sleeves 46 and 47, respectively, of a bag 41, and the upper, open end of the bag neck 45 is secured over a filler neck 34 by a collar 51, the bag is fully supported and capable of holding liquids without risk of collapsing. This process is repeated until each of the twenty-four spaces in divider rack 20 is occupied by a single bag 41, and each bag is similarly supported. When rack 20 has been thus filled with bags, the rack 10 with the loaded divider rack thereon may then be placed in known manner inside of a conventional fluid sampling device for the purpose of filling bags 41 with fluid samples via a nozzle (not illustrated) which, for example, may be rotatably indexed successively into registry with the upper ends of the filleer spouts 31.

Completion of the sampling procedure is followed by sealing each bag 41 closed in order to prevent contamination of its contents, and to accommodate, if necessary, for subsequent transportation thereof. Sealing may be accomplished by one of two effective means. First, if sample bags 41 are to be transported while they are still supported in divider rack 20, then a cap 56 (phantom lines in FIG. 3) may be releasably press fit over the top of each collar 51. Alternatively, if sample bags 41 are to be removed from base rack 10 and divider rack 20, then the collars 51 are disengaged from the necks 34 and the filler spouts 31 are removed from the dividers 25 to expose the open, upper ends of the necks 45 of the now-filled bags 41. The necks 45 may then be heat-sealed closed by a conventional, portable heat sealing device or the like. After being sealed closed the bags may be removed individually from divider rack 20, if they were separated prior to use, or the entire string of bags may be collectively handled by simply allowing them to remain on divider rack 20, which may be lifted off of the base rack 10.

In situations where the collected fluid samples must remain cooled, an ice cooler may be incorporated into the housing of a portable fluid sampling device, whereby an ice-water solution resides in intimate contact with each plastic bag 41 in rack 20 to facilitate proper heat exchange. Referring now to FIGS. 5 and 6, it becomes necessary in this situation to employ modified bags, such as the bag denoted at 41' in FIG. 6, and a bag spreader 60 of the type shown in FIG. 5. Each modified bag 41' has the same general configuration as plastic bags 41, but in addition, each bag 41' has formed on each lateral side thereof a pocket 49, which is open at its upper end. Each bag spreader 60 comprises a pair of folded, matching plates 61 and 62 that are joined together on their upper edges along a fold line 63. In use, as shown in FIG. 6, each bag spreader 60 is inserted over the upper edge of a divider 25 so that its plates 61 and 62 extend downwardly on opposite sides of the divider and into the pockets 49 of adjacent bags 41' so that the bags are spread open to prevent ice water in the rack 20 from collapsing the bags or from otherwise interfering with the delivery of sample fluids into the bags.

From the foregoing, it should be apparent that the present invention provides an improved fluid sample collector for use in a fluid sampling device. By utilizing containers in the form of light, disposable plastic bags, bulky sets of rigid sample bottles or containers become unnecessary, and therefore portable fluid sampling devices and their accessories become easier to transport. Also, the need for carefully washing sample bottles before reusing them is obviated. In addition, by producing the bags in continuous strip form, they can be successively numbered during the manufacture thereof, and if desired, they can remain connected to each other upon being mounted in the divider rack. The strips of bags may be wound on storage reels to be available when needed.

Although the present invention has been described in conjunction with disposable plastic bags 41, it should be noted that recyclable plastics may also be used for manufacture of such bags without departing from the scope of this invention. Moreover, if desired the plastic bags 41 could be connected together by web sections 48 extending only between their elongate side edges 44; and instead of sections 46 and 47 being tubular, they could be solid ribs disposed to be inserted into vertical grooves in pins 17 and 18. Also, although the preferred embodiment was described in conjunction with a divider rack 20 intended to support twenty-four storage containers, it should be noted that either larger or smaller plastic bags may be utilized for obtaining larger or smaller sized samples, and in such an event it may be necessary to reduce or increase, respectively, the number of plastic bags which are intended to be supported by the divider rack 20. Likewise, if differently sized or shaped bags are employed for collecting fluid samples, then a divider rack 20 with appropriately spaced and shaped dividers 25 and appropriately sized filler spouts 31 must also be employed.

While this invention has been illustrated and described in connection with only certain embodiments thereof, it will be apparent that it is capable of still further modification, and that this application is intended to cover any such modifications that may fall within the scope of one skilled in the art, or the appended claims.

I claim:

1. A fluid sample collector for storing liquid samples from an associated liquid sample dispenser in a plurality of like, plastic bags each of which has an opening in one end thereof, comprising
    a bag divider rack having thereon a bottom wall, and a plurality of dividers projecting vertically upwardly from said bottom wall in radially spaced relation to a centerline thereof, and angularly spaced from each other about said centerline,
    first bag supporting means for releasably supporting one of said plastic bags in each of the angular spaces formed between said angularly spaced dividers, and
    second bag supporting means including a plurality of filler spouts removably mounted on said dividers, and each of said spouts having therethrough an axial bore disposed to be releasably secured in communication with said opening in an adjacent one of said bags operatively to support said opening in position to register with said dispenser to receive a liquid sample therefrom.

2. A fluid sample collector as defined in claim 1, wherein
    said first bag supporting means comprises a plurality of pairs of radially spaced bag supporting elements, the two elements of each pair thereof being mounted adjacent the radially inner and outer ends, respectively, of a respective angular space between an adjacent pair of dividers, and with said elements projecting vertically above said bottom wall of said divider rack, and
    each of said bags has thereon spaced support sections releasably engagable with a pair of said supporting elements for supporting a bag upright in the space between an adjacent pair of said dividers.

3. A fluid sample collector as defined in claim 2, wherein
    each of said pairs of bag supporting elements comprises a pair of spaced, parallel pins the upper ends of which extend above said bottom wall of said rack, and
    said spaced support sections on each of said bags comprise a pair of spaced, parallel sleeves formed in each of said bags adjacent opposed side edges thereof, and disposed to be inserted slidably and removably over the upper ends of one of said pairs of said pins.

4. A fluid sample collector as defined in claim 1, including
    means for releasably connecting each of said spouts to a different one of said dividers adjacent the upper edge thereof, and with said bores in said spouts positioned in the spaces between said dividers and registering coaxially with the openings in said one ends of the plastic bags supported in said spaces, and
    an annular collar member removably mounted on each of said spouts coaxially of said bore therein, and releasably engagable with a portion of one of said bags coaxially of the opening therein operatively to secure said portion of said one bag between said collar and its associated spout.

5. A fluid sample collector as defined in claim 4, wherein
    each of said bags has thereon a tubular neck portion defining said opening in said one end thereof,
    said neck portion on each of said bags extends through said bore in the filler spout which registers therewith, and is folded rearwardly over the last-named spout coaxially of the bore therein, and
    each of said collar members is press fit over its associated spout and the portion of said neck portion of the bag which is folded thereover.

6. A fluid sample collector as defined in claim 4, wherein said means for releasably connecting each of said spouts to one of said dividers comprises a slot formed in the underside of each of said spouts in laterally spaced relation to said bore therein, and disposed to be inserted slidably and removably over said upper edge of one of said one dividers to be supported thereby in one of said angular spaces formed between said dividers.

7. A fluid sample collector as defined in claim 1, wherein
each of said dividers comprises a rigid plate,
each of said bags has thereon a pair of external pockets formed on respectively opposite sides thereof, and operatively supported by said first bag supporting means in confronting relation to the adjacent pair of divider plates that define the space in which a respective bag is supported, and
third bag supporting means is mounted on each of said divider plates and projects from opposite sides thereof into one of the pockets of each of the two bags separated by a respective divider plate.

8. A fluid sample collector as defined in claim 7, wherein
each of said pockets in the bags in said rack has an open end facing upwardly, and
said third bag supporting means comprises a plurality of brackets each of which is removably mounted on one of said divider plates and has on opposite ends thereof generally flat, planar sections projecting slidably into said open ends of a pair of said pockets positioned at opposite sides, respectively, of said one divider plate.

9. A fluid sample collector as defined in claim 3, wherein
said first bag supporting means further comprises a second rack having a bottom wall upon which the bottom wall of said bag divider rack is removably seated,
said bottom wall of said bag divider rack is in the shape of a ring having inner and outer peripheral surfaces disposed coaxially of said centerline, said dividers comprise a plurality of plates disposed in planes extending radially between said inner and outer peripheral surfaces, and
one of said two bag supporting pins of each pair thereof is secured at its lower end to said second rack adjacent the inner peripheral surface of said ring, and the other pin of each pair thereof is secured at its lower end to said second rack adjacent the outer peripheral surface of said ring.

10. A fluid sample collector as defined in claim 9, wherein
said one and said other pins, respectively, are arranged in circular arrays adjacent the inner and outer peripheral surfaces, respectively, of said ring, and
each of said racks has thereon a pair of handles for manipulating the racks manually.

11. A fluid sample colelctor for use in a device for dispensing fluid samples into a plurality of disposable fluid sample containers each of which has theron spaced container support sections and a mouth for accepting and pouring liquids, comprising
a base rack comprising a grid with a generally planar bottom wall and handles projecting therefrom,
container support means on said base rack releasably engagable with said support sections of said containers to support the containers on said rack with said mouths of the containers facing upwardly,
a divider rack having a bottom wall removably seated on the bottom wall of said base rack, and having thereon a plurality of divider plates projecting upwardly from said bottom wall thereof and between adjacent containers mounted on said base rack, and
FILLER means removably mounted on said divider plates for supporting said mouths of said containers in registry with a dispenser in said fluid sample dispensing device.

12. A fluid sample collector as defined in claim 11, wherein said fluid sample containers are pliable plastic bags each having said spaced support sections thereof formed as an integral part of a respective bag adjacent opposite sides of the mouth of the bag.

13. A fluid sample collector as defined in claim 12, wherein said spaced support sections on said bags comprise a pair of sleeves formed on each of said bags adjacent opposed side edges thereof.

14. A fluid sample collector as defined in claim 13, wherein each of said bags is connected to two adjacent bags of said plurality thereof.

15. A fluid sample collector as defined in claim 13, wherein said container support means comprises a plurality of pins projecting from said base rack releasably into the sleeves in said bags, and said mouths of said bags are engaged with said filler means on said divider plates.

16. A fluid sample collector as defined in claim 11, wherein
said filler means comprises an annular filler spout removably mounted on each of said divider plates,
each of said filler spouts has extending into a bottom surface thereof a slot for mounting each spout on one of said divider plates, and has a generally cylindrical neck projecting from a top surface thereof, and
an annular collar is attached to each spout by a filament and is disposed to be releasably engaged with said neck of the associated spout to attach the mouth of one of said containers thereto.

17. A fluid sample collector as defined in claim 16, wherein said mouth of each of said containers is disposed to be releasably secured between said neck and said collar of the associated spout, when said collar is releasably engaged with said neck.

18. A fluid sample collector as defined in claim 16, wherein the number of said filler spouts present in said collector is equal to the number of said containers supported on said base rack.

19. A method of collecting liquid samples in a cyclically operated fluid sample device having a dispensing nozzle which is indexed intermittently during each operating cycle of said device along a predetermined path in said device, and successively from one dispensing position to another in series thereof, comprising
providing in strip form a plurality of like, empty plastic bags equal in number to the number of dispensing positions in said series thereof, each of said bags having an opening in one end thereof, and successive bags in said strip thereof being connected to adjacent bags by severable sections of plastic,
prior to each operating cycle of said device removably supporting one of said empty bags in each of the dispensing positions in said device into which said nozzle is to be indexed, and with the opening in each empty bag positioned to register with the discharge end of said nozzle when the latter is indexed into a dispensing position,
sealing the opening in each of said bags after a liquid sample has been placed therein by said nozzle, and
at the end of each cycle of operation of said device removing the sealed bags from said dispensing positions in said device.

20. A method as defined in claim 19 including cutting through said severable sections of said adjacent bags to separate said bags from each other.

* * * * *